United States Patent [19]

DeLuca et al.

[11] Patent Number: 4,594,192
[45] Date of Patent: Jun. 10, 1986

[54] 2α-FLUOROVITAMIN D$_3$

[75] Inventors: Hector F. DeLuca, Madison, Wis.; Yoko Tanaka, Delmar, N.Y.; Nobuo Ikekawa; Yoshiro Kobayashi, both of Tokyo, Japan

[73] Assignee: Wisconsin Alumni Research Foundation, Madison, Wis.

[21] Appl. No.: 713,941

[22] Filed: Mar. 20, 1985

[51] Int. Cl.$^4$ .............................................. C07J 9/00
[52] U.S. Cl. ................................................ 260/397.2
[58] Field of Search ..................................... 260/397.2

[56] References Cited

U.S. PATENT DOCUMENTS 4,254,045  3/1981  DeLuca et al. ................... 260/397.2
4,307,025  12/1981  DeLuca et al. ................... 260/397.2

OTHER PUBLICATIONS

Journal of Labelled Compounds Radio-Pharm. (1984) England, vol. 21, No. 8, pp. 759–766, as Abstracted in Chem. Abstracts (1985) vol. 102, par 95,901f.

*Primary Examiner*—Elbert L. Roberts
*Attorney, Agent, or Firm*—Howard W. Bremer

[57] ABSTRACT

The invention provides new derivatives of vitamin D$_3$, 2α-fluorovitamin D$_3$ and the acylates thereof.

The compounds are characterized by vitamin D-like activity in their ability to increase intestinal calcium transport and serum calcium indicating their ready application as substitutes for vitamin D.

3 Claims, No Drawings

2α-FLUOROVITAMIN D₃

This invention was made with Government support under Grant No. AM-14881 awarded by the Department of Health and Human Services and U.S. Japan Cooprative Grant INT-8016902 awarded by the National Science Foundation.

TECHNICAL FIELD

This invention relates to a novel vitamin D compound.

More specifically this invention relates to a fluorinated derivative of vitamin $D_3$.

Vitamin D is known to regulate calcium and phosphorus metabolism in animals and humans. It is now also generally accepted that the physiological action of vitamin D is dependent on the metabolism of the vitamin to hydroxylated forms. Thus vitamin $D_3$ is hydroxylated in vivo to 25-hydroxyvitamin $D_3$ which in turn is converted to 1α,25-dihydroxyvitamin $D_3$, and it is the latter compound specifically which is thought to regulate calcium and phosphorus homeostasis by promoting calcium and phosphorus transport in intestine and the mobilization of bone mineral.

Because of their high biological activity, these hydroxylated forms of vitamin D are important pharmaceutical products which have found use in the treatment of various bone disorders. In addition, many unnatural analogs of these hydroxylated vitamin D metabolites have been prepared in recent years, including some highly potent fluorinated vitamin D derivatives.

BACKGROUND ART

Vitamin D metabolities, analogs and their preparation and application are discussed in many references in the patent and other literature, as for example, in U.S. Pat. No. 3,565,924 directed to 25-hydroxycholecalciferol; U.S. Pat. No. 3,697,559, directed to 1,25-hydroxycholecalciferol; U.S. Pat. No. 3,741,996 directed to 1α-hydroxycholecalciferol, and U.S. Pat. No. 3,907,843 directed to 1α-hydroxyergocalciferol. Fluorinated vitamin D derivatives and methods for preparing such compounds are the subject of U.S. Pat. No. 4,196,133 directed to 24,24-difluoro-25-hydroxyvitamin $D_3$; U.S. Pat. No. 4,201,881 directed to 24,24-difluoro-1α,25-dihydroxyvitamin $D_3$; U.S. Pat. Nos. 4,188,345, 4,229,357, 4,229,358, 4,226,787 and 4,224,230; U.S. Pat. Nos. 4,307,025 directed to 1α,25-dihydroxy-2β-fluorovitamin $D_3$, 4,358,406 directed to 26,26,25,27,27,27-hexafluoro-1α,25-dihydroxycholecalciferol, 4,254,045 directed to 1α-hydroxy-2β-fluorocholecalciferol, 4,248,791, directed to 25-hydroxy-26,26,26,27,27,27-hexafluorocholecalciferol.

DISCLOSURE OF INVENTION

New fluorinated vitamin D derivatives have now been found which exhibit vitamin D-like activity essentially equivalent to that of vitamin D as measured by stimulation of intestinal calcium transport and bone mobilization. These compounds are conveniently represented by the formula

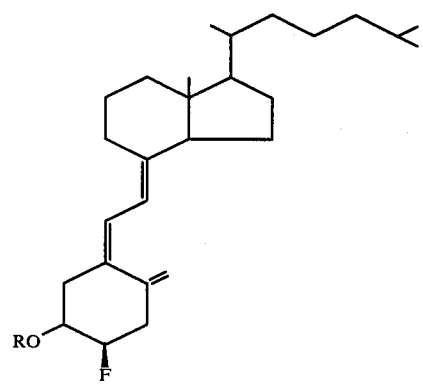

where R is hydrogen or O-acyl.

By virtue of their vitamin D-like activity these compounds would find application as a substitute for vitamin D in its various uses.

BEST MODE FOR CARRYING OUT THE INVENTION

The compounds of this invention can be prepared in accordance with the following description and abbreviated schematic diagram:

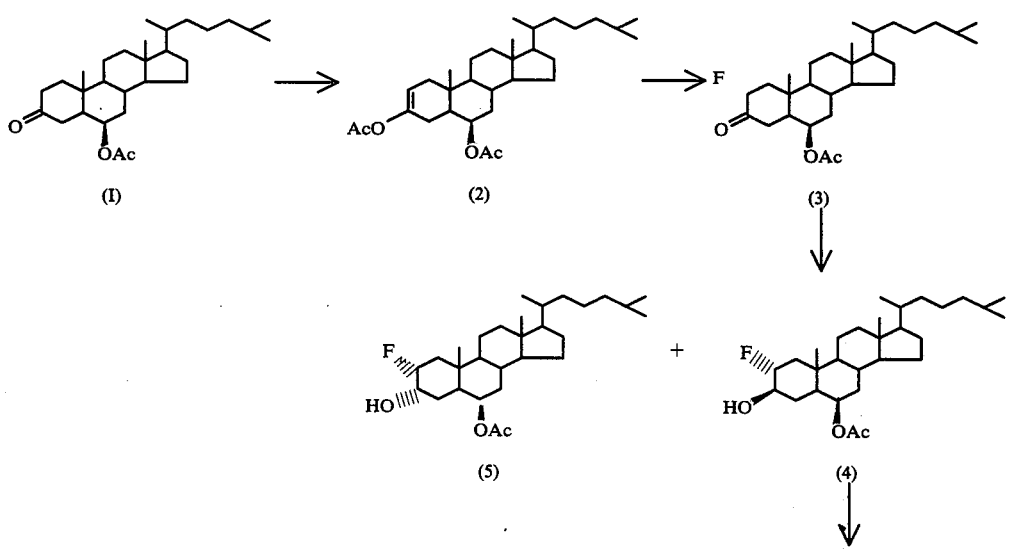

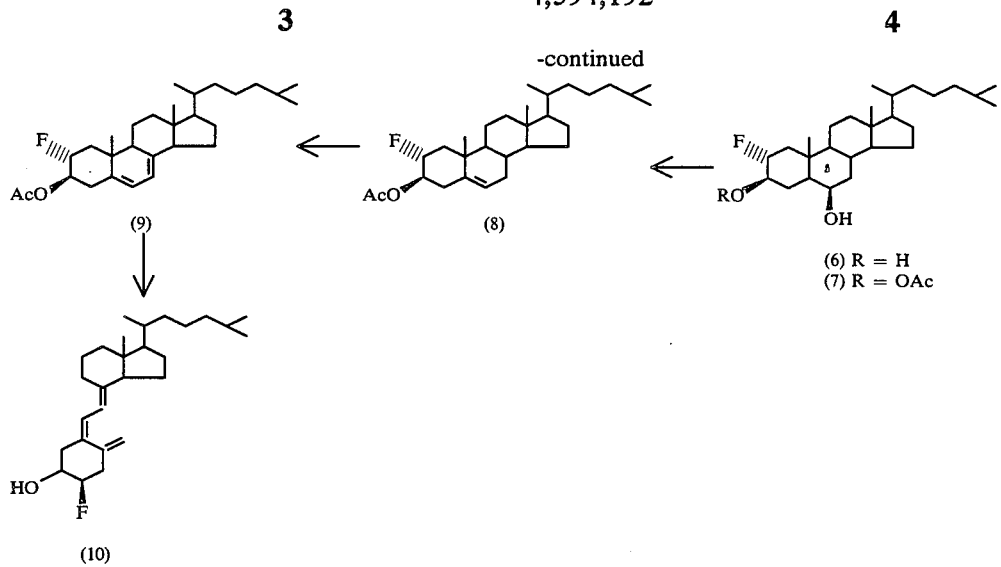

6β-acetoxycholestan-3-one (1) (prepared in accordance with the procedure set forth in B. Pelc et al, J. Chem. Soc. (C), 1624 (1970) was converted into the enol acetate (2) by treatment with isopropenyl acetate in the presence of p-toluenesulfonic acid.

The enol acetate (2) was treated with cesium fluoroxysulphate (S. Stauber et al, J. Chem. Soc., Chem. Comm. 148, 795 (1981)) in dry methylene chloride to afford 2α-fluoro-3-ketone (3), mp 153°–156° C. The α-orientation of the fluorine at C-2 position was expected from the reported data (D. H. R. Barton, L. S. Godinho, R. H. Hesse, and M. M. Pecket, Chem. Commun., 804 (1968). R. H. Hesse, Israel J. Chem., 17, 60 (1978). W. J. Middleton and E. M. Bingham, J. Sm. Chem. Sco., 102, 4845 (1980) and R. Filler, Israel J. Chem., 17 (1978). T. Tsushima, K.), and was confirmed by nmr data. Reduction of the fluoroketone (3) with sodium borohydride gave a mixture of the 2α-fluoro-3β-ol (4) (53%) and its 3α-epimer (5) (20%).

After alkaline hydrolysis of the 6-acetate (4), the 3-acetate (7) was prepared by acetic anhydride treatment. The dehydroxylation of (7) with POCl$_3$ in pyridine gave 3β-acetoxy-2α-fluorocholest-5-ene (8), mp 116°–118°.

Transformation of (8) into 2α-fluorovitamin D$_3$ (10) was carried out by the standard procedure: allylic bromation of (8) by N-bromosuccinimide and dehydrobromination with n-Bu$_4$NF afforded a mixture of the 4,6-diene and the 5,7-diene (9), from which the 5,7-diene was isolated by treatment with p-toluenesulfonic acid in acetone, followed by preparative thin layer chromatography.

The 5,7-diene (9) was irradiated with a medium pressure mercury lamp in a mixture of benzene-ethanol (2:1) for 2.5 min, and refluxed for 1 hr to give the corresponding vitamin D$_3$ acetate. Subsequent saponification and purification by HPLC afforded 2α-fluorovitamin D$_3$ (10).

SYNTHESIS OF 2α-FLUOROVITAMIN D$_3$

2,6β-Diacetoxycholest-2-ene (2)

A solution of 6β-acetoxycholestan-3-one (1) (1215 mg, 2.74 mmol) of isopropenyl acetate (15 ml) was refluxed in the presence of p-toluenesulfonic acid (20 mg) under argon for 3 hr. Most of the solvent was removed and the concentrated mixture was extracted with ethyl acetate. The extract was washed with saturated NaHCO$_3$, and brine, and dried over MgSO$_4$. The residue obtained upon evaporation of the solvent was purified by column chromatography on silica gel (40 g). Elution with benzene gave the enol-acetate (2) (1265 mg, 95%), glass; δ0.71(3H, s, 18-H$_3$), 0.88(6H, d, J=6 Hz, 26- and 27-H$_3$), 0.91(3H, d, J=6 Hz, 21-H$_3$), 1.02(3H, s, 19-H$_3$) 1.08 and 1.11 (6H, Sx2, 2- and 6-acetyl), 5.03(1H, m, 6α-H), and 5.23(1H, dd, J=5 and 2 Hz).

6β-Acetoxy-2α-fluorocholestan-3-one (3)

To a suspension of cesium fluoroxysulfate (713 mg) in dry methylene chloride (8 ml) was added the enol acetate 2 (1.4 g) in methylene chloride (8 ml) at room temperature and the mixture was stirred at room temperature for 24 hr. Water was added and the resulting precipitate was filtered off. The filtrate was extracted ith methylene chloride, and the extract was washed with brine and dried over MgSO$_4$. The residue obtained upon evaporation of the solvent was purified with a silica gel (130 g) column. Elution with hexane-ether (1:1) gave a mixture containing 2 as a major component (397 mg). Elution with hexane-ether (1:1) gave the fluoroketone (3) (308 mg, 23%), mp 153°–156° (from MeOH); NMR δ0.73(3H, s, 18-H$_3$), 0.87(6H, d, J=6 Hz, 26- and 27-H$_3$), 0.93(3H, d, J=6 Hz, 21-H$_3$), 1.27(3H, S, 19-H$_3$) 2.07(3H, s, acetyl), 4.97(1H, m, 6α-H), 5.02(1H, ddd, J=48.7, 12.4, and 7.0 Hz, 2β-H). m/z 402.3277(M+-AcOH). (C$_{27}$H$_{43}$FO requires M, 402.3296).

6β-Acetoxy-2α-fluoro-3β-hydroxycholestane (4)

To a solution of the fluoroketone (3) (270 mg) in THF (24 ml) was added sodium borohydride (90 mg) in methanol (6 ml) at room temperature and the mixture was stirred at room temperature for 1 hr. To the reaction mixture were added water and ethyl acetate and the excess reagent was quenched with 2N-HCl. The organic phase was washed with saturated NaHCO$_3$ and brine, and dried over MgSO$_4$. The crude mixture obtained upon evaporation of the solvent was separated by column chromatography on silica gel (10 g). Elution with benzene-ethyl acetate 10:1 gave 6β-acetoxy-2α-fluoro-3α-hydroxycholestane (5) 54 mg, 2%), mp 148°–150° (CHCl$_3$-MeOH); δ0.79(3H, s, 18-H$_3$), 2.20(3H, s, acetyl), 4.22(1H, m, $W_{1/2}=13$ Hz, $3\beta$-H), 4.65(1H, m, $2\beta$-H), and 4.98(1H, m, $6\alpha$-H); m/z, 404 (M+-AcOH), 389, 384, 371 and 369.

Further elution with the same solvent system gave the $3\beta$-alcohol (4) (144 mg, 53%), mp 142°–143° (CHCl$_3$-MeOH); $\delta$0.70(3H, s, 18-H$_3$), 0.86(6H, d, J=6 Hz, 26- and 27-H$_3$), 0.91(3H, d, J=6 Hz, 21-H$_3$), 103(3H, s, 19-H$_3$), 2.02(3H, s, acetyl), 3.70(1H, m, $W_{1/2}=30$ Hz, $3\alpha$-H), 4.49(1H, dm, J=54 Hz, $2\beta$-H) and 5.02(1H, m, $6\alpha$-H); m/z 404 (M+-AcOH), 389, 384, 371, and 369.

$3\beta$-Acetoxy-$2\alpha$-fluoro-$6\beta$-hydroxycholestane (7)

The $3\beta$-alcohol (4) (144 mg, 0.309 mmol) was treated with 5% KOH-methanol (15 ml) in THF (30 ml) at 60° for 4 hr. To the reaction mixture were added water and ethyl acetate. The organic phase was wash with 2N-HCl, saturated NaHCO$_3$, and brine and dried over MgSO$_4$. The residue obtained upon evaporation of the solvent, gave the diol (6). This was dissolved in a mixture of pyridine (10 ml) and acetic anhydride (2 ml), and the solution was stirred at −15° for 16 hr. The reaction mixture was extracted with ethyl acetate. The extract was washed with 2N-HCl, saturated NaHCO$_3$, and brine, and dried over MgSO$_4$. The residue obtained upon evaporation of the solvent was purified by silica gel column (10 g). Elution with benzene-ethyl acetate (10:1) gave the acetate (7) (132 mg, 92%), $\delta$3.90(1H, m, $6\alpha$-H), 4.96(1H, m, $3\alpha$-H).

$3\beta$-Acetoxy-$2\alpha$-fluorocholest-5-ene (8)

To the solution of the acetate (7) (92 mg, 0.198 mmol) in pyridine (2 ml) was added dropwise phosphorusoxychloride (0.06 ml) at 0° and the mixture was stirred at room temperature for 2 hr. To the reaction mixture were added ice and ethyl acetate. The organic phase was washed with 2N-HCl, saturated NaHCO$_3$ and brine, and dried over MgSO$_4$. The residue obtained upon evaporation of the solvent was purified by column chromatography on silica gel (5 g). Elution with benzene-ethyl acetate (20:1) gave the olefine (8) (90 mg, 98%), mp 116°–119° (MeOH); $\delta$0.68(3H s, 18H$_3$), 0.87(6H, d, J=6 Hz, 26- and 27-H$_3$), 0.93(3H, d, J=6 Hz, 21-H$_3$), 1.06(3H, s, 19-H$_3$), 2.08(3H, s, acetyl), 4.10–5.00(1H, broad, $2\beta$-H), 4.86(1H, m, $3\alpha$-H), and 5.42(1H, m, 6-H); m/z 386.3370(M+-AcOH). (CH$_{27}$H$_{43}$F required M, 386.3347).

$3\beta$-Acetoxy-$2\alpha$-fluorocholesta-5,7-diene (9)

To a refluxing solution of the olefin (8) (34.5 mg, 0.077 mmol) in carbon tetrachloride (2 ml) was added N-bromosuccinimide (19.2 mg), and the mixture was refluxed under argon. After 50 min, the reaction mixture was cooled and the precipitate was filtered off. Then the filtrate was concentrated under reduced pressure to give the crude bromide, which was treated in THF (5 ml) containing a small amount of tetrabutylammonium bromide at room temperature under argon in the dark. After 50 min, tetrabutylammonium fluoride (1 mol/l THF solution, 0.5 ml) was added, and the whole was stirred at room temperature for 30 min under argon in the dark. Water and ethyl acetate were added and the organic phase was washed with 2N-HCl, saturated NaHCO$_3$ and brine, and dried over MgSO$_4$. Evaporation of the solvent gave the crude diene, which was treated for 11 hr under argon in the dark with acetone (15 ml) containing a catalytic amount of $p$-toluenesulfonic acid. The reaction mixture was extracted with ethyl acetate. The extract was washed with saturated NaHCO$_3$, and brine, and dried over MgSO$_4$. The residue obtained upon evaporation of the solvent was applied on silica gel TLC-plate. The plate was developed with hexane-ethyl acetate (20:1) three times and elution of the scraped band (Rf=0.6) with ethyl acetate followed by evaporation of the solvent, gave the 5,7-diene (9) (8.4 mg, 25%), $\lambda_{max}$, 264, 272, 282, and 293 nm.

$2\alpha$-Fluorovitamin D$_3$ (10)

A solution of the 5,7-diene (5 mg) in benzene (80 ml) and ethanol (40 ml) was irradiated with a medium pressure mercury lamp through a Vicor filter for 2.5 min. at 0° under argon. The reaction mixture was then refluxed for 1 hr under argon. Evaporation of the solvent gave a crude mixture, which was applied to TLC-plates and developed with hexane-benzene (3:1) three times. The band (Rf=0.31) gave $2\alpha$-fluorovitamin D$_3$ (0.914 mg, 18.3%). This was treated with a mixture of 5% KOH-methanol (2 ml) and THF (2 ml) overnight at room temperature under argon in the dark. The reaction mixture was extracted with ethyl acetate. The extract was washed with 2N-HCl, saturated NaHCO$_3$ and brine, and dried over MgSO$_4$. Afer evaporation of the solvent, the residue was purified by HPLC (Shimadzu LC-3A; column, Zorbax-SIL, 4.6 mm i.d.×15 cm; eluent, hexane-methylene chloride 2:1; flow rate, 2.2 ml/min; retention time, 3.2 min) to give $2\alpha$-fluorovitamin D$_3$ (10), $\lambda_{max}$ 265, $\lambda_{min}$ 226 nm; $\delta$0.54(3H, s, 18-H$_3$), 0.87(6H, d, J=6 Hz, 26- and 27-H$_3$), 0.92(3H, d, J=6 Hz, 21-H$_3$), 3.88(1H, m, $3\alpha$-H), 4.46(1H, dm, J=48 Hz, $2\beta$-H), 4.96 and 5.16(2H, bs×2, 19-H), 5.91 and 6.30 (2H, ABq, J=11 Hz, 6- and 7-H); m/z 402.3272 (C$_{27}$H$_{43}$FO requires M, 402.3295).

Although in the foregoing description and schematic R is indicated as being hydrogen or O-acetyl it will be understood that other acyl groups would also find ready application, it being the intention that the term acyl as use in the specification and claims is intended to include acyl groups having from one to about four carbon atoms.

BIOLOGICAL ACTIVITY

The biological activity of $2\alpha$-Fluorovitamin D$_3$ was confirmed by appropriate in vivo assays in the rat. Male weanling rats were purchased from Holtzman Co., Wis. and fed ad libitum water and a low-calcium, vitamin D deficient diet as described by Suda et al (J. Nutrition 100:1049, 1970) for three weeks. The rats were then divided into three groups of five to six rats each and given respectively 250 ng of vitamin D$_3$ or 500 ng of $2\alpha$-fluorovitamin D$_3$ dissolved in 0.1 ml of 95% ethanol intrajugularly 24 hrs. prior to sacrifice. The rats in the control group were given the ethanol vehicle in the same manner. They were killed by decapitation and the blood was collected. Their duodena were immediately removed to measure the intestinal calcium transport activity by the method described by Martin and DeLuca (Am. J. Physiology 216, 1351, 1959). The blood was centrifuged to obtain serum. Serum calcium concentrations were determined in the presence of 0.1% lanthanum chloride with an atomic absorption spectrometer Model 403 (Perkin-Elmer Corporation, Norwalk, Conn.). Results are shown in Table 1.

TABLE 1

Biological activity of 2α-fluorovitamin $D_3$

| Compound administered | Intestinal calcium transport activity (Ca serosal/Ca mucosal) | Serum calcium concentration (mg/100 ml) |
|---|---|---|
| ethanol | 2.4 ± 0.2*[a] | 4.1 ± 0.1[c] |
| vitamin $D_3$ | 5.8 ± 0.4[b] | 5.6 ± 0.5[d] |
| 2α-fluorovitamin $D_3$ | 5.9 ± 1.1[b] | 5.6 ± 0.5[d] |

*standard deviation from the mean significantly different

[b] from [a] p 0.001

[d] from [c] P 0.001

It is evident from the data presented in Table 1 that 2α-fluorovitamin $D_3$ exhibits vitamin D-like activity essentially equivalent to that of vitamin $D_3$ itself.

We claim:

1. Compounds having the formula

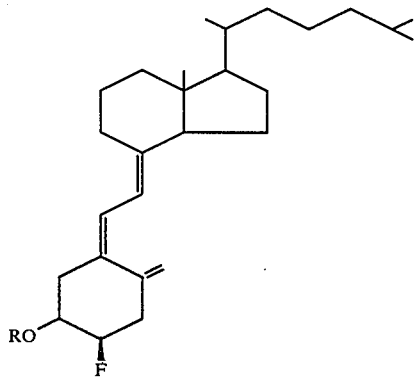

where R is hydrogen or O-acyl.

2. 2α-fluorovitamin $D_3$.

3. Compounds having the formula

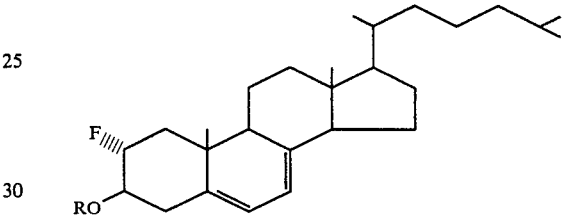

where R is hydrogen or O-acyl.

* * * * *